(12) United States Patent
Steinemann et al.

(10) Patent No.: US 7,087,085 B2
(45) Date of Patent: Aug. 8, 2006

(54) SURFACE-MODIFIED IMPLANTS

(75) Inventors: Samuel G. Steinemann, St. Sulpice (CH); James Parcival Simpson, Eptingen (CH)

(73) Assignee: Straumann Holding AG, Basel (CH)

( * ) Notice: Subject to any disclaimer, the term of this patent is extended or adjusted under 35 U.S.C. 154(b) by 13 days.

(21) Appl. No.: 10/333,859

(22) PCT Filed: Jul. 24, 2001

(86) PCT No.: PCT/CH01/00456

§ 371 (c)(1),
(2), (4) Date: Feb. 7, 2003

(87) PCT Pub. No.: WO02/07792

PCT Pub. Date: Jan. 31, 2002

(65) Prior Publication Data

US 2003/0176927 A1    Sep. 18, 2003

(30) Foreign Application Priority Data

Jul. 26, 2000    (CH)    ..................... 1481/00

(51) Int. Cl.
*A61F 2/28*    (2006.01)
(52) U.S. Cl. ................... 623/23.55; 427/2.26
(58) Field of Classification Search ............. 623/23.55, 623/23.53, 23.57, 23.76, 923, 11.11, 16.11, 623/17.11, 23.29, 23.36, 23.3; 427/2.26, 427/2.24, 2.14; 424/423
See application file for complete search history.

(56) References Cited

U.S. PATENT DOCUMENTS

| 4,973,493 | A | * | 11/1990 | Guire ........................ 427/2.24 |
| 5,080,924 | A | * | 1/1992 | Kamel et al. .............. 427/2.24 |
| 5,456,723 | A | | 10/1995 | Steinemann et al. |
| 5,646,134 | A | | 7/1997 | Yates |
| 5,733,564 | A | | 3/1998 | Lehtinen |
| 5,759,205 | A | * | 6/1998 | Valentini .................... 433/173 |
| 6,129,928 | A | * | 10/2000 | Sarangapani et al. ....... 424/423 |

FOREIGN PATENT DOCUMENTS

| EP | 1023910 | 1/1999 |
| WO | WO 92/09697 | 6/1992 |
| WO | WO 99/11202 | 3/1999 |
| WO | WO 00/44305 | 8/2000 |

\* cited by examiner

*Primary Examiner*—Pedro Philogene
(74) *Attorney, Agent, or Firm*—Kudirka & Jobse, LLP

(57) ABSTRACT

An osteogenic implant with improved osteointegration properties, this implant being made of titanium metal or a titanium-based alloy and being suitable for implantation in bones, said implant having a roughened surface, which in the hydroxylated state has been at least partially covered with a compound which comprises in the molecule at least two groups which are, independently of one another, a primary amino group, a secondary amino group, a carboxyl group, an amide group, a phosphano group and/or hydroxyl, or with a mixture of such compounds.

52 Claims, No Drawings

SURFACE-MODIFIED IMPLANTS

The present invention relates to surface-modified osteogenic implants which are used for insertion into bones and which display considerably improved osteointegration properties, and to processes for the production thereof.

Implants which are used for insertion into bones, such as, for example, hip or knee joint prostheses or pins to be screwed into the jaw to construct artificial teeth, are known per se. Such implants preferably consist of titanium or titanium-based alloys such as, for example, titanium/zirconium alloys, it being possible for the latter additionally to contain niobium, tantalum or other tissue-compatible metallic additions. The central properties of such implants are the strengths of the anchoring in the bone and the period of time in which integration is achieved. Osteointegration accordingly means a frictionally solid and permanent connection between implant surface and bone tissue.

The firmness of the anchoring of the implant in the bone can be established by mechanical measurements, namely by measuring the force, whether as pulling, pushing, shearing or torque, which is necessary in order to extract or unscrew the implant anchored in the bone from its anchoring, i.e. bring about a break of the adhesion between the surface of the implant and the bone substance connected thereto. Such measurement methods are known per se and described, for example, in Brunski, Clinical Materials, Vol. 10, 1992, pp. 153–201. Measurements have shown only little anchoring of titanium implants with a smooth surface structure in the bone, whereas implants with the roughened surface afford a noticeably improved bone-implant connection in relation to the tenacity.

EP 0 388 576 therefore proposes to apply to the implant surface in a first step a macro-roughness by means of sandblasting, and subsequently to superimpose a micro-roughness on the latter by means of treatment in an acid bath. The implants of this can thus be roughened by means of sandblasting and subsequently be treated with an etching agent, e.g. hydrofluoric acid or hydrochloric acid/sulfuric acid mixture. The surface provided with a defined roughness in this way is then cleaned with solvents and water and subjected to a sterilizing treatment.

The chemical state of the surface of titanium and titanium-based alloys is complex. It is assumed that the surface of titanium metal spontaneously oxidizes in air and water and thus a reaction with water then takes place on the surface, that is to say in the outermost atomic layer of the oxide, with formation of hydroxyl groups. This surface containing hydroxyl groups is referred to in the literature as "hydroxylated" surface. See H. P. Boehm, Acidic and Basic Properties of Hydroxylated Metal Oxide Surfaces, Discussions Faraday Society, Vol. 52, 1971, pp. 264–275.

It has now been found that a hydroxylated surface of surface-oxidized titanium metal or oxidized titanium-based alloy has bioactive properties, because the metallic foreign body forms a frictional connection with the bone tissue, that is to say undergoes osteointegration.

It has emerged, surprisingly, that such a hydroxylated and bioactive surface retains its activity over a longer period and unites with the bone substance to give a strong connection considerably more quickly than an identical surface which has not been treated according to the invention and it is normally dried in the air, when this hydroxylated surface has been treated with a compound which comprises in the molecule at least two groups which are, independently of one another, a primary amino group (—$NH_2$), a secondary amino group (—NH—), a carboxyl group (—COOH), an amide group (—C(O)NH—), a phosphono group (—P(O)(OH)$_2$) and/or hydroxyl, or with a mixture of such compounds, or this hydroxylated surface has been at least partially covered with such a compound or a mixture of such compounds. In this way an osteogenic implant with improved osteointegration properties, in particular also with an accelerated anchoring reaction, is obtained, and the bioactivity of the hydroxylated implant surfaces treated according to the invention remains substantially unchanged until the implant is inserted.

The present invention is defined in the claims. In particular, the present invention relates to a surface-modified osteogenic implant with improved osteointegration properties or with improved osteointegration, this implant consisting of titanium metal or a titanium-based alloy and having an at least partially roughened surface, characterized in that this surface in the hydroxylated state has been at least partially covered with a compound which comprises in the molecule at least two groups which are, independently of one another, a primary amino group, a secondary amino group, a carboxyl group, an amide group, a phosphono group and/or hydroxyl, or with a mixture of such compounds.

This compound preferably has a molecular weight not exceeding 2 000.

This surface is preferably stored enclosed in a gas- and liquid-tight envelope and in an atmosphere which is inert for the implant surface, that is to say that no compounds which are able to impair the bioactivity of the implant surface are present inside the envelope.

The inside of the envelope is preferably filled with gases which are inert for the implant surface, such as, for example, oxygen, nitrogen, noble gases or a mixture of such gases. The inside of the envelope may, however, also be at least partially filled with pure water which optionally contains additives, in which case the amount of water present is at least such that wetting of the roughened implant surface is ensured. The remaining volume inside the envelope can be filled with gases which are inert for the implant surface, such as, for example, oxygen, nitrogen, noble gases or a mixture of such gases.

The pure water present inside the envelope preferably comprises as additive or additives at least one compound which comprises in the molecule at least two groups which are, independently of one another, a primary amino group, a secondary amino group, a carboxyl group, an amide group, a phosphono group and/or hydroxyl, or a mixture of such compounds, that is to say at least one compound which can be used according to the invention for the treatment and at least partial covering of the implant surface.

The present invention also relates to processes for producing the implants of the invention and to the implants produced according to the invention.

The implants of the invention preferably consist of a titanium-based alloy, preferably of the titanium/zirconium alloy, it being possible for the latter additionally to contain niobium, tantalum or other tissue-compatible metallic additions. These implants are preferably used as hip or knee joint prostheses or as pins to be screwed into the jaw for constructing artificial teeth. Implants of this type, their characteristics and the metallic materials used to produce them are known per se and described, for example, in J. Black, G. Hastings, Handbook of Biomaterials Properties, pages 135–200, published by Chapman & Hall, London, 1998.

Investigations have shown that adequate anchoring of an implant in the bone depends to a large extent on the surface characteristics of the implant, especially on the roughness. According to the present invention, the bioactivity of the surface treated according to the invention supplements synergistically the essentially physical effect of the surface roughness, resulting in a considerable improvement in osteointegration. The tooth implant of the invention preferably has a macro-roughness such as, for example, a screw thread or recesses in the surface, which can be obtained for example by mechanical treatment and structuring, shot peening or sandblasting. In addition, this roughened surface preferably has a superimposed micro-roughness, this micro-roughness preferably being produced by chemical etching of the surface or by means of electrochemical (electrolytic) treatment or by a combination of these processes. This results in a surface which is hydroxylated and simultaneously also hydrophilic. This hydroxylated surface is treated according to the invention with a compound which comprises in the molecule at least two groups which are, independently of one another, a primary amino group, a secondary amino group, a carboxyl group, an amide group, a phosphono group and/or hydroxyl, or with a mixture of such compounds.

The hydroxylated surface can be produced for example by providing the surface with the desired roughness or texture, in particular by the implant surface being initially shot peened, sandblasted and/or roughened by use of plasma technology, and subsequently treating the mechanically roughened surface with an electrolytic or chemical process until a hydroxylated and hydrophilic surface is produced. The implant is preferably etched with an inorganic acid or a mixture of inorganic acids, preferably with hydrofluoric acid, hydrochloric acid, sulfuric acid, nitric acid or a mixture of such acids or else the surface is activated with hydrochloric acid, hydrogen peroxide and water in the ratio of about 1:1:5 by weight.

The procedure is preferably such that
the implant is shot peened and subsequently etched with dilute hydrofluoric acid at room temperature and washed with pure distilled and $CO_2$-free water; or
the implant is sandblasted, e.g. with alumina particles having an average particle size of 0.1–0.25 mm or 0.25–0.5 mm and subsequently treated with a hydrochloric acid/sulfuric acid mixture at elevated temperature and washed with pure distilled and $CO_2$-free water; or
the implant is sandblasted with coarse particles, e.g. with a particle mixture as previously defined, and subsequently treated with a hydrochloric acid/nitric acid mixture and washed with pure distilled and $CO_2$-free water; or
the implant is treated with a mixture of hydrogen chloride, hydrogen peroxide and water in the ratio of about 1:1:5 by weight and washed with pure distilled and $CO_2$-free water; or
the implant is roughened by using plasma technology and subsequently hydroxylated in a mixture of hydrogen chloride, hydrogen peroxide and water in the ratio of about 1:1:5 by weight and washed with pure distilled and $CO_2$-free water; or
the implant is treated in an electrolytic process, the surface having previously been roughened mechanically where appropriate, and subsequently washed with pure distilled and $CO_2$-free water.

In all cases, the implant or its hydroxylated surface is treated according to the invention directly with a compound which comprises in the molecule at least two groups which are, independently of one another, a primary amino group, a secondary amino group, a carboxyl group, an amide group, a phosphono group and/or hydroxyl, or with a mixture of such compounds. In particular, the implant or its hydroxylated surface is not treated with alcohol, acetone or another organic solvent or a disinfectant or exposed to the atmosphere or gaseous substances such as, for example, hydrocarbons, which are not inert for the hydroxylated and hydrophilic surface and reduce or destroy for example the hydrophilic surface property. The "pure" water used in the process contains neither carbon dioxide nor vapors of hydrocarbons, and no alcohols such as methanol or ethanol, and no acetone or related ketones. However, it may comprise specific additives as described hereinafter.

The "pure" water used for washing is preferably water which has been distilled several times or prepared by inverse osmosis and which has preferably been prepared in an inert atmosphere, that is to say, for example, under reduced pressure, in a nitrogen or noble gas atmosphere. In particular, the pure water has an electrical resistance of at least 2 mohmcm (electrical resistance >2 mohmcm) and a total organic carbon content (total organic carbon, TOC) not exceeding 10 ppb ($\leq 10$ ppb).

Subsequent to the washing process, the resulting implant is preferably stored in pure water which may optionally comprise additives. The resulting implant is preferably stored in a closed envelope which is filled with a gas which is inert for the implant surface, for example nitrogen, oxygen or noble gas, such as, for example, argon, and/or in pure water which optionally contains additives, until further processing according to the invention. The envelope is preferably virtually impermeable for gases and liquids.

The implant which has a hydroxylated surface, or the hydroxylated surface of the implant, is treated according to the invention in the hydroxylated state with a compound which comprises in the molecule at least two groups which are, independently of one another, a primary amino group, a secondary amino group, a carboxyl group, an amide group, a phosphono group and/or hydroxyl, or with a mixture of such compounds, and at least partially covered with such a compound or a mixture of such compounds. These compounds may furthermore also comprise one or more hydrosulfide groups (—SH). Such compounds must be pharmaceutically approved for the intended pharmaceutical purpose.

The compounds preferred for the treatment of the hydroxylated implant surface comprise in the molecule at least two groups which are, independently of one another, a primary amino group, a secondary amino group, a carboxyl group, an amide group and/or phosphono group. Further preferred compounds are those which comprise in the molecule at least two groups which are, independently of one another, a primary amino group, a secondary amino group, a carboxyl group and/or an amide group. Particularly preferred compounds are those which comprise in the molecule at least two such groups which are different from one another. Preference is given to phosphonium compounds, amino acids and polyamino acids, especially amino acids and polyamino acids. The molecular weight of these compounds is, as already mentioned, preferably in the range up to 2 000, preferably in the range from 60 to 1 500, preferably in the range from 200 to 1 100.

Compounds which have at least one primary and/or at least one secondary amino group are, for example, ethylenediamine, trimethylenediamine, compounds of the formula
$H_2N[(CH_2)_{1-3}NH]_{1-4}(CH_2)_{1-3}NH_2$, such as $H_2NCH_2CH_2NHCH_2CH_2$ related or homologous compounds. Compounds which have at least one primary and/or at least one secondary amino group and at least one hydroxyl group are, for example, ethanolamine, diethanolamine, triethanolamine and related or homologous compounds.

Compounds having at least one carboxyl group and at least one hydroxyl group are, for example, hydroxy carboxylic acids having 1–12 C-atoms, such as glycolic acid, beta-hydroxypropionic acid, beta-hydroxybutyric acid, gamma-hydroxybutyric acid or 6-hydroxycaproic acid.

Compounds having at least one carboxyl group and at least one amino group are, for example, the amino acids known per se, such as glycine, alanine, valine, leucine, phenylalanine, tyrosine, proline, hydroxyproline, serine, threonine, cysteine, cystine, tryptophan, aspartic acid, glutamic acid, arginine, lysine, histidine, and the other amino acids known per se. Further examples are gamma-aminobutyric acid or the aminosalicylic acid.

Compounds having at least one amide group are, for example, low molecular weight polyamino acids (polypeptides), preferably low molecular weight polyamino acids which are composed of, for example, 2 to 10 amino acids, preferably of 3, 5 or 7 amino acids. A very large number of such polyamino acids is known, such as, for example, Lys-Lys-Arg, Arg-Gly-Asp, Leu-Gly-Asp, Leu-Asp-Val, Gly-Arg-Gly-Asp-Ser, Gly-Arg-Gly-Asp-Tyr, Val-Arg-Gly-Asp-Glu, Val-Arg-Gly-Asp-Phe, Arg-Glu-Asp-Arg-Val, Arg-Gly-Asp-Phe-Val, Arg-Gly-Asp-Phe-Lys, Arg-Gly-Asp-Ser-Lys, Arg-Ala-Asp-Phe-Val, Tyr-Ile-Gly-Ser-Asp, Ile-Lys-Val-Ala-Val, Arg-Glu-Asp-Arg-Val, Asp-Gly-Glu-Ala-Lys, Lys-Gln-Ala-Gly-Asp, Gly-Arg-Gly-Asp-Ser-Pro-Cys, Phe-His-Arg-Arg-Ile-Lys-Ala. Preferred polyamino acids have the sequences Arg-Gly-Asp, or Leu-Asp-Val, or Arg-Glu-Asp-Arg-Val, or Phe-His-Arg-Arg-Ile-Lys-Ala. Suitable polyamino acids are likewise low molecular weight protein fractions like those resulting in a production of vegetable or animal gelatin. Polypeptides which are particularly suitable are those having a minimum distance between implant surface and the reactive end group of at least about 3.5 nm (nanometers).

Also suitable are polyamino acids in cyclic form, for example cyclo(Arg-Gly-Asp-[D-Phenylalanine]-Lys), or cyclo(Arg-Gly-Asp-[D-Valine]-Lys) or cyclo[D-Val-Arg-Gly-Asp-Glu(-∈Ahx-Tyr-Cys-NH$_2$-], which are preferably connected to a linear peptide having an anchor group. The polyamino acids may also be linked to other spacers, for example by reaction with epsilon-aminohexanoic acid or a polymer of this acid, for example dimeric or trimeric forms or by reaction with 3-mercaptobutyric acid, or with ethylene glycol units or diethylene glycol units. Radicals of the formula (—NH—CH$_2$CH$_2$OCH$_2$CH$_2$OCH$_2$C(O)OH) and similar radicals are also suitable as terminal groups.

Also suitable are hydroxamic acids of the formula R—C(O)NHOH, in which R is [HO(CH$_2$CH$_2$O)$_{1-4}$(CH$_2$)$_{1-4}$]—. Within the meaning of the present invention, hydroxamic acids are included among compounds which have an amide group (—C(O)NH—). Compounds having a phosphono group are, for example, compounds of the formula R$_1$—P(O)(OH)$_2$, in which R$_1$ is [HO(CH$_2$CH$_2$O)$_{1-4}$(CH$_2$)$_{1-4}$]—. Examples of such compounds are formula HOCH$_2$CH$_2$(OCH$_2$CH$_2$)$_2$OCH$_2$C(O)NHOH or HOCH$_2$CH$_2$(OCH$_2$CH$_2$)$_2$ OCH$_2$P(O)(OH)$_2$.

The aforementioned compounds which comprise in the molecule at least two groups which are, independently of one another, a primary amino group, a secondary amino group, a carboxyl group, an amide group, a phosphono group and/or hydroxyl preferably have a molecular weight no greater than 2 000, preferably in the range from 60 to 1 500, and preferably in the range from 200 to 1 100.

Many of the abovementioned compounds can be described as compounds of the general formula (I):

$$(A)_p(C_nH_{2n+2-p-r})(B)_r \qquad (I),$$

in which
the individual substituents A in the same molecule are, independently of one another, carboxyl, phosphono, —C(O)NHOH, phenyl, hydroxyphenyl, 4-imidazolyl, guanidino and/or 3-indolyl; preferably carboxyl, phosphono, phenyl, hydroxyphenyl, 4-imidazolyl, guanidino and/or 3-indolyl;
the individual substituents B in the same molecule are, independently of one another, hydroxyl, amino (—NH—/NH$_2$), amido (—C[O]NH—), hydroxymethyl (—CH$_2$OH) and/or hydrosulfide (—SH); preferably hydroxyl, amino and/or amido;
n is an integer from 1 to 12, preferably 1 to 8, preferably 1, 2, 3 or 4;
p is zero, 1, 2 or 3;
r is zero, 1, 2 or 3;
the total of [p+r] is an integer from 2 to 6, preferably from 2, 3 or 4;
2n+2−p−r is at least 1, preferably at least 2. The radical (C$_n$H$_{2n+2-p-r}$) is preferably linear or isopropyl.

Also suitable are compounds of the general formula (II) and of the formula (IIa):

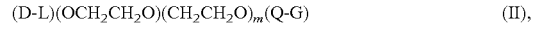

$$(D-L)(OCH_2CH_2O)(CH_2CH_2O)_m(Q-G) \qquad (II),$$

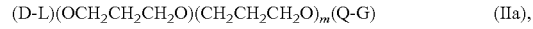

$$(D-L)(OCH_2CH_2O)(CH_2CH_2CH_2O)_m(Q-G) \qquad (IIa),$$

in which
the individual substituents D in the same molecule are, independently of one another, carboxyl, phosphono, or —C(O)NHOH or one of the meanings of G; preferably carboxyl, phosphono, or —C(O)NHOH; preferably carboxyl or phosphono;
the individual substituents G in the same molecule are, independently of one another, hydrogen, amino (—NH$_2$), amido (—C(O)NH$_2$), hydroxymethyl (—CH$_2$OH), hydrosulfide (—SH) or one of the meanings of D; preferably hydrogen, amino, amido, hydroxymethyl, hydrosulfide; preferably hydrogen, amino or amido;
L and Q are, independently of one another, the direct linkage, or a linker to link the substituents D and/or G, preferably —(C$_n$H$_{2n}$)— in which n is an integer from 1 to 8, preferably —CH$_2$— or —CH$_2$CH$_2$—;
m is zero, or an integer from 1 to 8, preferably zero, 1, 2, 3, 4 or 5, preferably zero or 1, preferably zero.

L and Q are the direct linkage preferably for G=hydrogen or hydroxymethylene. L and Q are preferably —(C$_n$H$_{2n}$)— for the other meanings of D and G.

Examples of compounds of the formula (II) have already been mentioned in the preceding sections.

Preference is given to amino acids and polyamino acids, especially polyamino acids which have the sequence Arg-Gly-Asp, such as Arg-Gly-Asp itself, Gly-Arg-Gly-Asp-Ser or Arg-Gly-Asp- Arg-Gly-Asp.

Methods for characterizing and analyzing metal surfaces are known per se. These methods can also be used for measuring and checking or monitoring the covering density. Such analytical methods known per se are, for example, infrared spectroscopy, laser desorption mass spectroscopy (LDMS), X-ray-excited photoelectron spectroscopy (XPS), matrix-assisted laser desorption ion mass spectroscopy (MALDI), time of flight secondary ion mass spectroscopy (TOFSIMS), electron and ion microanalysis, optical waveguide light mode spectroscopy (OWLS) or X-ray photoelectron diffraction (XPD) use. It can be used to measure for example the titanium atoms or hydroxyl groups available on the metal surface. The metal atoms or hydroxyl groups available on the metal surface ordinarily provide the maximum covering density of the surface with a monomolecular layer ("monolayer"). The stated analytical methods known per se can be used to measure the concentration and the thickness of the monomolecular layer, which depends in particular on the chemical composition of the metal surface, the pretreatment thereof and the chemisorbed compound. Thus, for example, titanium oxide has about four to five reactive, with an acidic or basic reaction, groups per $nm^2$ of surface. This means that the surface of titanium oxide can be covered with about four molecules of an amino acid or polyamino acid per $nm^2$ of surface. It is preferred according to the invention for there to be only about 5%–70% coverage, based on the maximum coverage of the metal surface with a monomolecular layer of the stated compound. It is particularly preferred according to the invention for the coverage to be 10%–50% and, in particular, about 20%, based on the maximum coverage of the metal surface with the monomolecular layer. In this sense, the metal surface continues to remain at least partially hydroxylated, through the remaining "free" hydroxyl groups, so that a combination of the two effects affords an implant with very good osteointegration properties.

The compound which comprises in the molecule at least two groups which are, independently of one another a primary amino group, a secondary amino group, a carboxyl group, an amide group, a phosphono group and/or hydroxyl, or with a mixture of such compounds, is applied to the hydroxylated surface of the implant in a suitable method, for example from aqueous solution or from an organic solvent or else by means of spraying with the pure compound or the pure compound mixture. The compound is thus adsorbed and bound by the hydroxylated surface. Bound means in this connection that it cannot be removed directly by rinsing with water. It is sufficient in this connection for the compound to be brought into contact with the hydroxylated metal surface in aqueous or organic solution of very low concentration, depending on the compound, in a choncentration of the order of 0.01 μmol/l (micromole per liter) or higher, for example 0.01 μmol/l to about 100 μmol/l, preferably 0.1 μmol/l up to about 10 μmol/l, preferably about 1 μmol/l, in order to produce a desired coverage. These concentration limits are, however, not critical. The covering density of the surface which is achieved with the said compounds is determined in particular by the concentration thereof in the liquid carrier, the contact time and the contact temperature, and the acid values (pH values) used.

In this sense, the present invention also relates to a process for producing an implant of the invention, by the implants surface being shot peened, sandblasted and/or roughened by use of plasma technology, characterized in that subsequently (i) the surface which has been roughened mechanically or by plasma technology is treated with an electrolytic or chemical etching process until a hydroxylated surface has been produced, preferably with an inorganic acid or a mixture of inorganic acids, preferably with hydrofluoric acid, hydrochloric acid, phosphoric acid, nitric acid, or a mixture of such acids, or hydrogen chloride, hydrogen peroxide and water in the ratio of about 1:1:5 by weight; and (ii) the surface is at least partially covered with an above-mentioned compound which comprises at least two groups, or with a mixture of such compounds.

The coverage of the hydroxylated metal surface with the said compound, or with the said compound mixture, can be explained by a chemisorption or by a chemical binding. This means that a reactive group of the added compound enters into a condensation reaction with the hydroxyl group present on the metal surface, for example in accordance with the formula: $\equiv TiOH + -CH_2C(O)OH \rightarrow \equiv TiOC(O)CH_2- + H_2O$, where $\equiv Ti-$ is a metal ion on the metal surface. An amphoteric character may be ascribed to the surface depending on the acid value of the electrolytes surrounding the surface, there being an interaction between the acid in the electrolyte and the hydroxyl with a basic reaction on the oxide surface, or the anion in the electrolyte and the hydroxyl with an acidic reaction in the oxide. The surface reactions can be explained through the formation of covalent bonds, electrostatic effects and/or the formation of hydrogen bonds. The present invention is not, however tied to these explanations. The decisive fact is that the surface treatment described herein preserves and improves the bioactivity of the hydroxylated surface.

In order to bind the said compound which comprises in the molecule at least two groups, or a mixture of these compounds, to the metal surface, the procedure is preferably such that the compound is applied from aqueous or organic solution, preferably from aqueous solution, by wetting, or by spraying with the pure compound, to the surface. There is, where appropriate, heating to a temperature of about 70° C. to 120° C., where appropriate under pressure. The binding of the compound to the surface can likewise be promoted with UV radiation. A further method consists of applying the compound, depending on the nature of the compound, from aqueous acidic or basic solution to the surface. In this case, the solution preferably has an acid value (pH value) of between 2 and 4 or between 8 and 11. The implant can subsequently be heated where appropriate to a temperature of about 70° C. to 120° C., where appropriate under pressure, or treated with UV radiation.

The implant of the invention, but at least its surface coverage according to the invention, is preferably enclosed in a gas- and liquid-tight envelope, there being no compounds inside the envelope which are able to impair the bioactivity of the implant surface, that is to say are inert for the implant surface. This gas- and liquid-tight envelope is preferably a sealed ampoule made of glass, metal, a synthetic polymer or another gas- and liquid-tight material or a combination of such materials. The metal is preferably in the form of a thin metal sheet, it being possible to combine polymeric materials and metallic sheets, but also glass, in a manner known per se with one another to give a suitable packaging.

It is preferred for there to be an inert atmosphere inside the envelope and for it to be filled with an inert gas and/or at least partially with pure water which optionally contains additives. A suitable additive which can be added according to the invention to the pure water for improved storage of the implant is, in particular, a compound which comprises in the molecule at least two groups which are, independently of one another, a primary amino group, a secondary amino group, a carboxyl group, an amide group, a phosphono group and/or hydroxyl, or a mixture of such compounds, and in particular the same compound or the same mixture of compounds with which the implant surface has been covered. In this case, the pure water contains the said compound or the mixture of compounds preferably in a concentration in the range from about 0.01 µmol/l to 100 µmol/l, preferably about 0.1 µmol/l to 10 µmol/l and preferably in a concentration of about 1 µmol/l.

Further suitable additions which can be added according to the invention to the pure water are monovalent alkali metal cations such as $Na^+$ or $K^+$, or a mixture of $Na^+$ and $K^+$, with appropriate anions in the form of inorganic salts, such as, for example, sodium chloride, potassium chloride, sodium or potassium chlorate, sodium or potassium nitrate, sodium or potassium phosphate or a mixture of such salts. It is likewise also possible to add divalent cations in the form of water-soluble inorganic salts. Suitable cations are, in particular, $Mg^{+2}$, $Ca^{+2}$ $Sr^{+2}$ and/or $Mn^{+2}$ in the form of the chlorides, chlorates, nitrates or mixtures thereof. Suitable inorganic anions are also phosphate and phosphonate anions, by which are meant in each case also monoorthophosphate anions and diorthophosphate anions, and monoorthophosphonate anions and diorthophosphonate anions, in combination with the cations mentioned.

Preferred inorganic cations and anions are those which already occur in body fluid, especially in the respective physiological concentration and with a physiological acid value in the range of preferably 4 to 9 and preferably with an acid value in the range of 6 to 8. Preferred cations are $Na^+$, $K^+$, $Mg^{+2}$ and $Ca^{+2}$. The preferred anion is $Cl^-$. The total amount of said cations and anions is preferably in each case in the range from about 50 mEq/l to 250 mEq/l, preferably about 100 mEq/l to 200 mEq/l and preferably about 150 mEq/l . Here, Eq/l means (formula) equivalent weight, and Eq/l corresponds to the atomic weight of the formula unit divided by the valency. mEq/l means milliequivalent weight per liter. If the envelope contains divalent cations, in particular $Mg^{+2}$, $Ca^{+2}$, $Sr^{+2}$ and/or $Mn^{+2}$, alone or in combination with the monovalent cations mentioned, then the total amount of the divalent cations present is preferably in the range from 1 mEq/l to 20 mEq/l. It is likewise possible for the abovementioned organic compounds to be present in a mixture with the stated inorganic salts dissolved in pure water, in which case the stated concentrations for the additions which are present still apply and are usually sufficient.

Methods for measuring the effective surface area of a metallic body are known per se. Thus, for example, electrochemical measurement methods are known and are described in detail in P. W. Atkins, Physical Chemistry, Oxford University Press, 1994. It is also possible to obtain the effective surface area from roughness measurements as the square of the hybrid parameter $L_r$, i.e. the square of the profile-length ratio. The parameter $L_r$ is defined in the standard DIN 4762 as the ratio of the length of the extended two-dimensional profile and of the measured distance. However, the precondition for the latter measurement is that the vertical and lateral resolution of the measurement method is less than 1 µm and is in fact close to 0.1 µm.

The reference area for all these measurement methods is the flat polished metal surface. The measured values for the roughened surface compared with those on the flat and polished surface indicate how much greater the roughened surface is, compared with the flat and polished surface. In vitro investigations with bone cells and in vivo histomorphometric investigations on implants of the invention indicate that the osteogenic properties of the implants of the invention are particularly high when the roughened surface is preferably at least 1.5 times and preferably at least twice as large as the comparable flat and polished surface. The roughened implant surface is preferably at least 2 to 12 times as large, and preferably about 2.5 to 6 times as large, as the comparable flat and polished surface.

Industrially produced surfaces of titanium and titanium alloys for processing in laboratories and clinics usually have impurities which consist essentially of carbon compounds and traces of nitrogen, calcium, sulfur, phosphorus and silicon. These impurities are concentrated in the outermost metal oxide layer. The hydroxylated and hydrophilic implant surface preferably contains not more than 20 atom % carbon measured by spectroscopic methods such as XPS or AES or other spectroscopic methods known per se.

The following examples illustrate the invention.

EXAMPLE 1

A) A conventional form of a tooth implant in the form of a screw with a diameter of 4 mm and a length of 10 mm was produced. The basic form was obtained by removing material by turning and milling the cylindrical preform in a manner known per se. The surface to be inserted into the bone was then provided with a macro-roughness as described in EP 0 388 576 by sandblasting it with particles of average particle size 0.25–0.50 mm. Subsequently, the roughened surface (macro-roughness) was treated with an aqueous hydrochloric acid/sulfuric acid mixture with an $HCl:H_2SO_4:H_2O$ ratio of 2:1:1 at a temperature above 80° C. for about five minutes to result in a ratio of the roughened implant surface to the comparable polished surface of 3.6, measured by voltametry in an aqueous electrolyte with 0.15M NaCl, (corresponding to a ratio of 3.9 measured by impedance spectrometry in 0.1 molar $Na_2SO_4$ electrolyte). The implant formed in this way was washed with pure water.

B) Subsequently, the implant obtained in section A) was boiled in a solution consisting of pure water which contained the compound $(HO)_2(O)P(CH_2)_4COOH$ (prepared in a manner known per se) in a concentration of 100 µmol/l in the acidic solution in a Soxhlet apparatus under nitrogen for two hours. The implant was removed and washed with pure water under nitrogen. Measurements revealed a coverage of about 30% of the metal surface. The implant was subsequently a) sealed directly in a glass ampoule which was filled with pure water, opened after 4 weeks and implanted;

b) sealed directly in a glass ampoule which was filled with pure water which was adjusted to pH=9 with 0.2M sodium bicarbonate and contained the pentapeptide Gly-Arg-Gly-Asp-Ser in a concentration of 1 µmol/l. The glass ampoule was opened after 4 weeks, briefly washed in isotonic saline and implanted;

c) after completion of the treatment as in section A) dried in atmospheric air and implanted (comparative test).

The implants obtained as in tests a), b) and c) were implanted into the upper jaw of a minipig. The anchoring in the bone was measured as the loosening torque of the screw implanted in the upper jaw of the minipig. The results obtained are indicated in table 1.

TABLE 1

|  | Anchoring* after 2 weeks (Ncm) | Anchoring* after 3 weeks (Ncm) | Anchoring* after 4 weeks (Ncm) |
| --- | --- | --- | --- |
| Test a) | 30 | 70 | 120 |
| Test b) | 40 | 90 | 130 |
| Comparative test c) | 20 | 60 | 100 |

*The anchoring is indicated as loosening torque in Ncm (averages).

The results in tests a) and b) (implants of the invention) show that the corresponding loosening torques for the stated incorporation times are distinctly higher than those of test c). These show shorter incorporation times and an accelerated osteointegration.

EXAMPLE 2

A) The surface of the implant was prepared as described in example 1, section A).

B) Subsequently, the implant obtained in section A) was boiled in a solution consisting of pure water which contained the compound $HOCH_2CH_2(OCH_2CH_2)_2OCH_2C(O)NHOH$ (prepared in a manner known per se) in a concentration of 10 µmol/l in the acidic solution in a Soxhlet apparatus under nitrogen for two hours. The implant was removed and washed with pure water under nitrogen. Measurements revealed a coverage of about 20% of the metal surface. The implant was subsequently d) sealed directly in a glass ampoule which was filled with pure water, opened after 4 weeks and implanted;

e) sealed directly in a glass ampoule which was filled with pure water which was adjusted to pH=9 with 0.2M sodium bicarbonate and contained the cyclic pentapeptide Asp-Ser-Lys-Arg-Gly in a concentration of from 0.1 to 1 µmol/l. The glass ampoule was opened after 4 weeks, briefly washed in isotonic saline and implanted;

f) after completion of the treatment as in section A) dried in atmospheric air and implanted (comparative test).

The implants obtained as in tests d), e) and f) were implanted into the upper jaw of a minipig. The anchoring in the bone was measured as the loosening torque of the screw implanted in the upper jaw of the minipig. The results obtained are virtually coincident with the values given in table 1.

EXAMPLE 3

Example 1 was repeated but with the proviso that the compound $(HO)_2(O)P(CH_2)_4COOH$ in section B) was replaced by the pentapeptide Gly-Arg-Gly-Asp-Ser. Results analogous to those in table 1 were obtained.

EXAMPLE 4

Example 2 was repeated but with the proviso that the compound $HOCH_2CH_2(OCH_2CH_2)_2OCH_2C(O)NHOH$ in section B) was replaced by the cyclic pentapeptide Asp-Ser-Lys-Arg-Gly. Results analogous to those in table 1 were obtained.

EXAMPLE 5

Examples 1 to 4 [in each case sections A) and B)] were repeated but with the proviso that an implant with a ratio of the roughened implant surface to the comparable polished surface of 1.9 (measured by impedance spectrometry in 0.1 molar $Na_2SO_4$ electrolyte) was produced. For this purpose, the implant surface was cut only mechanically, by turning, and subsequently etched as indicated in example 1. The implant obtained in this way was washed with pure water. Subsequently, the implant was g) sealed directly in a glass ampoule which was filled with pure water which was adjusted to pH=9 with 0.2M sodium bicarbonate and contained the pentapeptide Gly-Arg-Gly-Asp-Ser in a concentration of from 0.1 to 1 µmol/l. The glass ampoule was opened after 4 weeks, briefly washed in isotonic saline and implanted;

h) dried with atmospheric air and implanted (comparative test).

The implants obtained in tests g) and h) were implanted in the upper jaw of the minipig. The anchoring in the bone was measured as the loosening torque of the screw implanted in the upper jaw of the minipig. The results obtained are indicated in table 2.

TABLE 2

|  | Anchoring* after 2 weeks (Ncm) | Anchoring* after 3 weeks (Ncm) | Anchoring* after 4 weeks (Ncm) |
| --- | --- | --- | --- |
| Test g) | 25 | 45 | 70 |
| Comparative test h) | 15 | 30 | 60 |

*The anchoring is indicated as loosening torque in Ncm (averages).

The results of test g) (implant of the invention) show that the corresponding loosening torques for the stated incorporation times are distinctly higher than those in test h). If it is assumed that a loosening torque of at least 35 Ncm is regarded as absolutely necessary in dental surgery for constructing a superstructure, this value is achieved by the implant of the invention after three weeks at the latest.

EXAMPLE 6

Tests analogous to examples 1 and 2 were carried out by in each case replacing the compound $(HO)_2(O)P(CH_2)_4COOH$ (from example 1) and the compound $HOCH_2CH_2(OCH_2CH_2)_2OCH_2C(O)NHOH$ (from example 2) by glycine (molecular weight [MW]: 75.07), serine (MW:105.09) lys.lys.arg (MW: 466.58), aminosalicylic acid, ethylenediamine and lactic acid. In these cases, results analogous to those indicated in table 1 were obtained.

The invention claimed is:

1. An osteogenic implant made of titanium metal or a titanium-based alloy, having an at least partially roughened surface, which in a hydroxylated state, is at least partially covered with a compound comprising at least two independent groups selected from a primary amino group, a secondary amino group, a carboxyl group, an amide group, a hydroxyl group, and combinations thereof, wherein said surface area is from 5% to 70% covered with said compound, based on a maximum coverage of said surface with a molecular layer.

2. An osteopenic implant as claimed in claim 1, wherein said surface is from 10% to 50% covered with said compound based on the maximum coverage of said surface with a molecular layer.

3. An implant as claimed in claim 1, wherein said surface has at least partially free hydroxyl groups.

4. An implant as claimed in claim 1, wherein said implant is constructed of a titanium/zircon alloy.

5. An implant as claimed in claim 1, wherein said implant has a macro-roughness and a micro-roughness superimposed on said macro-roughness.

6. An implant as claimed in claim 1, wherein said compound comprises at least two compounds selected from hydroxy carboxylic acids having 1–12 C atoms.

7. An implant as claimed in claim 1, wherein said compound comprises at least two groups selected from low molecular weight polyamino acids.

8. An implant as claimed in claim 7, wherein at least one of said polyamino acids represents a low molecular weight protein fraction like low molecular weight protein fractions that result in the production of vegetable or animal gelatin.

9. An implant as claimed in claim 7, wherein at least one of said polyamino acids is a cyclic polyamino acid.

10. An implant as claimed in claim 1, wherein said compound comprises at least two groups selected from hydroxy carboxylic acids having 1–12 C atoms and compounds having a phosphono group.

11. An implant as claimed in claim 4, wherein said titanium/zircon alloy comprises niobium, tantalum or other tissue-compatible metallic additions.

12. An implant as claimed in claim 5, wherein said micro-roughness is produced by chemical etching of said surface, electrolytic treatment or combinations thereof.

13. An implant as claimed in claim 12, wherein said etching is achieved with one or more inorganic acids selected from hydrochloric acid, sulfuric acid, nitric acid and combinations thereof.

14. An implant as claimed in claim 9, wherein said cyclic polyamino acid is connected to a linear peptide having an anchor group or is linked to a spacer.

15. An implant as claimed in claim 14, wherein said spacer is linked by reaction with epsilon-aminohexanoic acid, a polymer thereof or 3-mercaptobutyric acid.

16. An implant as claimed in claim 7, wherein said low molecular weight polyamino acids are composed of 2 to 10 amino acids.

17. An osteogenic implant made of titanium metal or a titanium-based alloy, having an at least partially roughened surface, which, in a hydroxylated state is at least partially covered with a compound comprising at least two independent groups which are, independently of one another, selected from a primary amino group, a secondary amino group, a carboxyl group, an amide group, a phosphono group and/or a hydroxyl group and combinations thereof, wherein said surface is from 5% to 70% covered with the said compound based on a maximum coverage of said surface with a monomolecular layer.

18. An implant as claimed in claim 17, wherein said surface is about 20% covered with said compound based on the maximum coverage of said surface with a molecular layer.

19. An osteogenic implant made of titanium metal or a titanium-based alloy, having an at least partially roughened surface, which in a hydroxylated state, is at least partially covered with a compound comprising at least two independent groups selected from a primary amino group, a secondary amino group, a carboxyl group, an amide group, a hydroxyl group, and combinations thereof, wherein said compound comprises at least two compounds selected from ethylenediamine, trimethylene-diamine; compounds of the formula $H_2N[(CH_2)_{1-3}NH]_{1-4}(CH_2)_{1-3}NH_2$ and related or homologous compounds, ethanolamine, diethanolamine, triethanolamine and related or homologous compounds.

20. An implant as claimed in claim 19, wherein at least one of said compounds of the formula $H_2N[(CH_2)_{1-3}NH]_{1-4}(CH2)_{1-3}NH_2$ is $H_2NCH_2CH_2NHCH_2NH_2$.

21. An osteogenic implant made of titanium metal or a titanium-based alloy, having an at least partially roughened surface, which in a hydroxylated state, is at least partially covered with a compound comprising at least two independent groups selected from a primary amino group, a secondary amino group, a carboxyl group, an amide group, a hydroxyl group, and combinations thereof, wherein said compound comprises at least two groups selected from low molecular weight polyamino acids, and wherein at least one of said polyamino acids has a sequence of Arg-Gly-Asp, Leu-Asp-Val, Arg-Glu-Asp-Arg-Val or Phe-His-Arg-Arg-Ile-Lys-Ala.

22. An osteogenic implant made of titanium metal or a titanium-based alloy, having an at least partially roughened surface, which in a hydroxylated state, is at least partially covered with a compound comprising at least two independent groups selected from a primary amino group, a secondary amino group, a carboxyl group, an amide group, a hydroxyl group, and combinations thereof, wherein said compound comprises at least two groups selected from low molecular weight polyamino acids, and wherein at least one of said polyamino acids has a minimum distance between said surface and a reactive end group of at least 3.5 nm.

23. An osteogenic implant made of titanium metal or a titanium-based alloy, having an at least partially roughened surface, which in a hydroxylated state, is at least partially covered with a compound comprising at least two independent groups selected from a primary amino group, a secondary amino group, a carboxvl group, an amide group, a hydroxyl group, and combinations thereof, wherein said compound comprises at least two groups independently or in combination, having a molecular weight no greater than 2000.

24. An implant as claimed in claim 23, wherein said molecular weight ranges from 60 to 1500.

25. An osteogenic implant made of titanium metal or a titanium-based alloy, having an at least partially roughened surface, which in a hydroxylated state, is at least partially covered with a compound comprising at least two independent groups selected from a primary amino group, a secondary amino group, a carboxyl group, an amide group, a hydroxyl group, and combinations thereof, wherein said compound comprises at least two groups of the formula (I):

wherein:
  independent substituents of A in the same molecule are selected from: carboxyl, phosphono, —C(O)NHOH, phenyl, hydroxyphenyl, 4-imidazolyl, guanidino, 3-indolyl, and combinations thereof;
  independent substituents of B in the same molecule are selected from: hydroxyl, amino (—NH—/NH$_2$), amido (—C[O]NH—), hydroxymethylene (—CH$_2$OH), hydrosulfide (—SH—) and combinations thereof;
  n is an integer from 1 to 12,
  p is zero, 1, 2 or 3;
  r is zero, 1, 2 or 3;
  a sum of p and r is an integer from 2 to 6, and 2n+2−p−r is at least 1.

26. An osteogenic implant made of titanium metal or a titanium-based alloy, having an at least partially roughened surface, which in a hydroxylated state, is at least partially covered with a compound comprising at least two independent groups selected from a primary amino group, a secondary amino group, a carboxyl group, an amide group, a hydroxyl group, and combinations thereof, wherein said compound comprises at least two groups of the formulae:

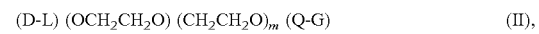

or

wherein:
  independent substituents of D in the same molecule are, selected from carboxyl, phosphono, —C(O)NHOH, one selected from substituents of G and combinations thereof;
  independent substituents of G in the same molecule are selected from hydrogen, amino (—NH$_2$), amido (—C(O)NH$_2$), hydroxymethylene (—CH$_2$OH), hydrosulfide (—SH—), one selected from said substituents of D and combinations thereof;

L and Q are, independently of one another, the direct linkage, or a linker to link to one or both of said substituents D and G; and m is zero or an integer from 1 to 8.

27. An implant as claimed in claim 26, wherein L and Q are $(C_nH_{2n})$—wherein n is an integer from 1 to 8.

28. An implant as claimed in claim 26, wherein L and Q are —OH$_2$— or, CH$_2$CH$_2$—.

29. An osteogenic implant made of titanium metal or a titanium-based alloy, having an at least partially roughened surface, which in a hydroxylated state, is at least partially covered with a compound comprising at least two independent groups selected from a primary amino group, a secondary amino group, a carboxyl group, an amide group, a hydroxvl group, and combinations thereof, wherein at least said covered surface thereof is enclosed in a gas- and liquid-tight envelope filled with a gas that is inert for said surface and/or partially with water.

30. An implant as claimed in claim 29, wherein said water contains an envelope compound comprising in the molecule, at least two independent groups selected from a primary amino group, a secondary amino group, a carboxyl group, an amide group, aphosphono group, a hydroxyl, and combinations thereof.

31. An implant as claimed in claim 29, wherein said water contains a compound comprising, in molecular form, at least two independent groups, in a concentration ranging from 0.01 μmol/l to 100 μmol/l.

32. An implant as claimed in claim 29, wherein said water contains inorganic salts in the form of monovalent alkali metal cations, with appropriate anions and/or divalent cations in the form of water-soluble inorganic salts.

33. An implant as claimed in claim 32, wherein said water contains inorganic salts in a total amount of said cations and anions ranging from 50 mEq/l to 250 mEq/l.

34. An implant as claimed in claim 29, wherein said water contains additives.

35. An implant as claimed in claim 30, wherein said envelope compound corresponds to said compound on said surface.

36. A method of making an osteogenic implant made of titanium metal or a titanium-based alloy, having an at least partially roughened surface, which in a hydroxylated state, is at least partially covered with a compound comprising at least two independent groups selected from a primary amino group, a secondary amino group, a carboxyl group, an amide group, a hydroxyl group, and combinations thereof, wherein said surface is shot peened, sandblasted and/or roughened by use of plasma technology, comprising:

treating said surface with an electrolytic or chemical etching process until a hydroxylated surface has been produced; and covering said surface from 5% to 70% with a compound comprising at least one group selected from a primary amino group, a secondary amino group, a carboxyl group, an amide group, a phosphono group and combinations thereof based on a maximum coverage of said surface with a molecular layer.

37. The method as claimed in claim 36, wherein said compound comprises, in molecular form at least two independent groups selected from a primary amino group, a secondary amino group, a carboxyl group, an amide group, a phosphono group, a hydroxyl, and combinations thereof; said method further comprising:

applying said compound on said surface an aqueous solution, by wetting or spraying: and heating said compound to a temperature of about 80° C. to 120° C., where appropriate under pressure.

38. The method as claimed in claim 36, wherein said compound is brought into contact with said surface in an aqueous solution in a concentration of at least 10 μmol/l.

39. The method of claim 36, wherein said treating is achieved with an inorganic acid or a mixture of inorganic acids selected from hydrofluoric acid, hydrochloric acid, phosphoric acid, nitric acid and mixtures thereof, or hydrogen chloride, hydrogen peroxide and water in the ratio of about 1:1:5 by weight.

40. A method for implanting an osteogenic implant made of titanium metal or a titanium-based alloy, having an at least partially roughened surface, which in a hydroxylated state, is at least partially covered with a compound comprising at least two independent groups selected from a primary amino group, a secondary amino group, a carboxyl group, an amide group, a hydroxyl group, and combinations thereof, wherein at least said covered surface thereof is enclosed in a gas- and liquid-tight envelope filled with a gas that is inert for said surface and/or partially with water, comprising removing said osteogenic implant from said envelope immediately before implanting.

41. An osteogenic implant made of titanium metal or a titanium-based alloy, having an at least partially roughened surface, which in a hydroxylated state, is at least partially covered with a compound comprising at least two independent groups selected from a primary amino group, a secondary amino group, a carboxyl group, an amide group, a hydroxyl group, and combinations thereof, wherein said compound comprises at least two groups selected from low molecular weigh polyamino acids, wherein at least one of said polyamino acids is a cyclic polyamino acid and wherein said cyclic polyamino acid is cyclo(Arg-Gly-Asp-[D-valine]-Lys) or cyclo[D-Val-Arg-Gly-Asp-Glu(-∈Ahx-Tyr-Cys-NH2-].

42. An osteogenic implant made of titanium metal or a titanium-based alloy, having an at least partially roughened surface, which in a hydroxylated state, is at least partially covered with a compound comprising at least two independent groups selected from a primary amino group, a secondary amino group, a carboxyl group, an amide group, a hydroxyl group, and combinations thereof, wherein said compound comprises at least two groups selected from low molecular weight polyamino acids, wherein at least one of said polyamino acids is a cyclic polyamino acid and wherein said cyclic polyamino acid has as a terminal group a radical of the formula (—NH—CH$_2$CH$_2$OCH$_2$C(O)OH).

43. An osteogenic implant made of titanium metal or a titanium-based alloy, having an at least partially roughened surface, which in a hydroxylated state, is at least partially covered with a compound comprising at least two independent groups selected from a primary amino group, a secondary amino group, a carboxyl group, an amide group, a hydroxyl group, and combinations thereof, wherein said compound comprises at least two compounds selected from hydroxy carboxylic acids having 1–12 C atoms and wherein at least one of said hydroxy carboxylic acids having 1–12 C atoms is selected from glycolic acid, beta-hydroxy-proprionic acid, beta-hydroxybutyric acid, gamma-hydroxy-butyric acid, 6-hydroxycaproic acid, amino acids, aminosalicylic acid and combinations thereof.

44. An implant as claimed in claim 43, wherein said amino acids are selected from glycine, alanine, valine, leucine, phenylalanine, tyrosine, proline, hydroxyproline, serine, threonine, cystein, cytine, tryptophan, aspartic acid, glutamic acid, arginine, lysine, histidine, gamma-aminobutyric acid and combinations thereof.

45. An osteogenic implant made of titanium metal or a titanium-based alloy, having an at least partially roughened surface, which in a hydroxylated state, is at least partially covered with a compound comprising at least two independent groups selected from a primary amino group, a secondary amino group, a carboxyl group, an amide group, a hydroxyl group, and combinations thereof, wherein said compound comprises at least two groups selected from low molecular weight polyamino acids, and wherein said low molecular weight polyamino acids are selected from Lys-Lys-Arg, Arg-Gly-Asp, Leu-Gly-Asp, Leu-Asp-Val, Gly-Arg-Gly-Asp-Ser, Gly-Arg-Gly-Asp-Tyr, Val-Arg-Gly-Asp-Glu, Val-Arg-Gly-Asp-Phe, Arg-Glu-Asp-Arg-Val, Arg-Gly-Asp-Phe-Val, Arg-Gly-Asp-Phe-Lys, Arg-Gly-Asp-Ser-Lys, Arg-Ala-Asp-Phe-Val, Tyr-Ile-Gly-Ser-Asp, Ile-Lys-Val-Ala-Val, Arg-Glu-Asp-Arg-Val, Asp-Gly-Glu-Ala-Lys, Lys-Gln-Ala-Gly-Asp, Gly-Arg-Gly-Asp-Ser-Pro-Cys, Phe-His-Arg-Arg-Ile-Lys-Ala and combinations thereof.

46. An osteogenic implant made of titanium metal or a titanium-based alloy, having an at least partially roughened surface, which in a hydroxylated state, is at least partially covered with a compound comprising at least two independent groups selected from a primary amino group, a secondary amino group, a carboxyl group, an amide group, a hydroxyl group, and combinations thereof, wherein said compound comprises at least two groups selected from hydroxy carboxylic acids having 1–12 C atoms and compounds having a phosphono group and wherein said hydroxy carboxylic acids having 1–12 C atoms are of the formula R—C(O)NHOH, wherein R is $[HO(CH_2CH_2O)_{1-4}CH_2)_{1-4}]—$.

47. An implant as claimed in claim 46, wherein said R—C(O)NHOH is $HOCH_2CH_2(OCH_2CH_2)_2OCH_2C(O)NH)OH$.

48. An osteogenic implant made of titanium metal or a titanium-based alloy, having an at least partially roughened surface, which in a hydroxylated state, is at least partially covered with a compound comprising at least two independent groups selected from a primary amino group, a secondary amino group, a carboxyl group, an amide group, a hydroxyl group, and combinations thereof, wherein said compound comprises at least two groups selected from hydroxy carboxylic acids having 1–12 C atoms and compounds having a phosphono group and, wherein said compounds having a phosphono group are of the formula $R_1—P(O)(OH)_2$, wherein $R_1$ is $[HO(CH_2CH_2O)_{1-4}(CH_2)_{1-4}]—$.

49. An osteogenic implant made of titanium metal or a titanium-based alloy, having an at least partially roughened surface, which in a hydroxylated state, is at least partially covered with a compound comprising at least two independent groups selected from a primary amino group, a secondary amino group, a carboxyl group, an amide group, a hydroxyl group, and combinations thereof, wherein said compound comprises at least two groups selected from hydroxy carboxylic acids having 1–12 C atoms and compounds having a phosphono group and, wherein said phosphono group is of the formula $HOCH_2(OCH_2CH_2)_2OCH_2P(O)(OH)_2$.

50. An osteogenic implant made of titanium metal or a titanium-based alloy, having an at least partially roughened surface, which in a hydroxylated state, is at least partially covered with a compound comprising at least two independent groups selected from a primary amino group, a secondary amino group, a carboxyl group, an amide group, a hydroxyl group, and combinations thereof, wherein said surface is shot peened, sandblasted and/or roughened by use of plasma technology, comprising:

treating said surface with an electrolytic or chemical etching process until a hydroxylated surface has been produced; and covering said surface from 5% to 70% with a compound comprising at least one group selected from a primary amino group, a secondary amino group, a carboxyl group, an amide group, a phosphono group and combinations thereof based on a maximum coverage of said surface with a molecular layer.

51. The osteogenic implant as claimed in claim 50, wherein said compound comprises, in molecular form at least two independent groups selected from a primary amino group, a secondary amino group, a carboxyl group, an amide group, a phosphono group, a hydroxyl, and combinations thereof;

wherein said surface is shot peened, sandblasted and/or roughened by use of plasma technology comprising:

applying said compound on said surface an aqueous solution, by wetting or spraying: and heating said compound to a temperature of about 80° C. to 120° C., where appropriate under pressure.

52. The osteogenic implant as claimed in claim 50, wherein said osteogenic implant is made by bringing the compound into contact with said surface in an aqueous solution in a concentration of at least 50 µ mol/l.

* * * * *

UNITED STATES PATENT AND TRADEMARK OFFICE
CERTIFICATE OF CORRECTION

PATENT NO. : 7,087,085 B2  
APPLICATION NO. : 10/333859  
DATED : August 8, 2006  
INVENTOR(S) : Steinemann et al.

Page 1 of 2

It is certified that error appears in the above-identified patent and that said Letters Patent is hereby corrected as shown below:

At column 14, line 56, the eleventh line of claim 26 should read:
$\quad$ (D-L) (OCH$_2$CH$_2$CH$_2$O) (CH$_2$CH$_2$CH$_2$O)$_m$(Q-G) $\hspace{2cm}$ (IIa)

At column 15, line 8, the second line of claim 28 should read:
$\quad$ are —CH$_2$— or, —CH$_2$CH$_2$—.

At column 15, line 23, the fifth line of claim 30 should read:
$\quad$ amide group, a phosphono group, a hydroxyl, and combina- At column 15, line 67, the eighth line of claim 37 should read:
$\quad$ solution, by wetting or spraying; and At column 16, line 33, the ninth line of claim 41 should read:
$\quad$ molecular weight polyamino acids, wherein at least one of At column 16, line 37, the thirteenth line of claim 41 should read:
$\quad$ Cys-NH$_2$-].

At column 17, line 32, the twelfth line of claim 46 should read:
$\quad$ R—C(O)NHOH, wherein R is [HO(CH$_2$CH$_2$O)$_{1-4}$ ( At column 17, line 36, the third line of claim 47 should read:
$\quad$ NHOH.

At column 18, line 41, the tenth line of claim 51 should read:
$\quad$ solution by wetting or spraying; and At column 18, line 42, the eleventh line of claim 51 should read:
$\quad$ heating said compound to a temperature of about 80°C At column 18, line 43, the twelfth line of claim 51 should read :
$\quad$ to 120°C, where appropriate under pressure.

UNITED STATES PATENT AND TRADEMARK OFFICE
CERTIFICATE OF CORRECTION

PATENT NO. : 7,087,085 B2
APPLICATION NO. : 10/333859
DATED : August 8, 2006
INVENTOR(S) : Steinemann et al.

It is certified that error appears in the above-identified patent and that said Letters Patent is hereby corrected as shown below:

At column 18, line 47, the fourth line lf claim 52 should read;
  solution in a concentration of at least 10 μmol/l.

Signed and Sealed this

Eighteenth Day of September, 2007

JON W. DUDAS
*Director of the United States Patent and Trademark Office*